United States Patent
Lim et al.

[11] Patent Number: 5,849,042
[45] Date of Patent: Dec. 15, 1998

[54] HAIR DYE COMPOSITIONS CONTAINING 2,3 DIALKYL-4-AMINOPHENOL AND A 2-ALKYL-1-NAPHTHOL

[75] Inventors: Mu-Ill Lim, Trumbull; Yuh-Guo Pan, Stamford, both of Conn.

[73] Assignee: Bristol-Myers Squibb, New York, N.Y.

[21] Appl. No.: 972,978

[22] Filed: Nov. 19, 1997

[51] Int. Cl.$^6$ ....................................................... A61K 7/13
[52] U.S. Cl. ........................................ 8/408; 8/421; 8/424
[58] Field of Search ................................ 8/408, 421, 424

[56] References Cited

U.S. PATENT DOCUMENTS

| | | | |
|---|---|---|---|
| 4,023,926 | 5/1977 | Bugant et al. | 8/407 |
| 4,692,166 | 9/1987 | Junino et al. | 8/410 |
| 4,865,619 | 9/1989 | Junino et al. | 8/412 |
| 5,279,620 | 1/1994 | Junino et al. | 8/409 |
| 5,344,464 | 9/1994 | Madrange et al. | 8/410 |

FOREIGN PATENT DOCUMENTS

| | | |
|---|---|---|
| 294669 | 7/1991 | European Pat. Off. . |
| 370880 | 11/1992 | European Pat. Off. . |
| 465339 | 12/1993 | European Pat. Off. . |
| 465340 | 12/1993 | European Pat. Off. . |
| 459900 | 1/1994 | European Pat. Off. . |
| 428441 | 8/1994 | European Pat. Off. . |
| 428442 | 8/1994 | European Pat. Off. . |
| 502784 | 6/1995 | European Pat. Off. . |
| 424261 | 1/1996 | European Pat. Off. . |
| 605320 | 4/1997 | European Pat. Off. . |
| 2234476 | 1/1973 | Germany . |

*Primary Examiner*—Paul Lieberman
*Assistant Examiner*—Caroline D. Liott
*Attorney, Agent, or Firm*—Morton S. Simon

[57] ABSTRACT

A 2-Substituted-1-naphthol of the formula:

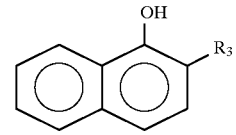

wherein $R_3$ is $C_1$–$C_6$ alkyl or monohydroxy $C_1$–$C_6$ alkyl couples with a primary intermediate of the formula:

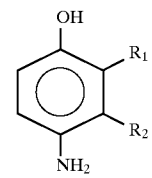

wherein $R_1$ and $R_2$ are each independently $C_1$–$C_6$ alkyl to produce an oxidative dye.

11 Claims, No Drawings

HAIR DYE COMPOSITIONS CONTAINING 2,3 DIALKYL-4-AMINOPHENOL AND A 2-ALKYL-1-NAPHTHOL

FIELD OF THE INVENTION

The present invention relates to oxidative keratinous dyeing compositions based on 2,3-dialkyl-4-aminophenols and 2-alkyl-1-naphthol.

BACKGROUND OF THE INVENTION

The developer, 2,3-dimethyl-4-aminophenol has been frequently mentioned in publications on hair dyeing as a part of an extensive list of 4-aminophenol derivatives, (see e.g. EP 605320, EP 502784, EP 465340 and EP 465339, EP 459900, EP 428442, EP 428441, EP 424261, DE 3030473, EP 370880, EP 294469, DE 3818139, DE 3609504, US 4023926, DE 2331548 and DE 2234476).

U.S. Pat. No. 5,344,464 discloses hair dye compositions and methods utilizing 2-substituted-1-naphthol couplers. 2-Substituted-1-naphthol is taught to impart a long lasting intense cosmetically desirable red color to hair. A list of 4-aminophenol derivatives contains 2-methyl-4-aminophenol, 3-methyl-4-aminophenol, 2,6-dimethyl-4-aminophenol, 2,5-dimethyl-4-aminophenol and 5-aminosalicylic acid. 2,3-Dimethyl-4-aminophenol was not mentioned in this patent.

The usefulness of 2,3-dimethyl-4-aminophenol has not been demonstrated in the prior art. Actual working examples utilizing this primary intermediate cannot be found in the patents.

SUMMARY OF THE INVENTION

The present invention relates to a dyeing composition for keratinous fibers, and in particular for human keratinous fibers, said composition comprising 2,3-dialkyl-4-aminophenol and 2-alkyl-1-naphthol and to a dyeing process using such composition.

DETAILED DESCRIPTION OP THE INVENTION

Dyes produced by coupling of 2,3-dimethyl-aminophenol with 2-$C_1$-$C_6$-alkyl or $C_1$-$C_6$ monohydroxyalkyl-1-naphthol, particularly 2-methyl-1-naphthol, surprisingly impart vivid violet color to hair, in contrast to magenta color produced by the dye resulting from coupling of 2,6-dimethyl-4-aminophenol (example 1, below). Since these two primary intermediates (2,3-dimethyl-4-aminophenol vs. 2,6-dimethyl-4-aminophenol) are positional isomers, it was unexpected that the colors obtained when coupled with the same coupler were so different from each other.

The hair color obtained is very similar to that which results from dyeing hair with a dye produced by coupling p-phenylenediamine and 2-methyl-5-aminophenol. This finding advantageously allows one skilled in the art to formulate dark red and burgundy shades without relying on p-phenylenediamine. This is very important because the use of p-phenylenediamine is currently being questioned for toxicological reasons (see U.S. Pat. No. 5,538,516). For example, a combination of 2,3-dimethyl-4-aminophenol, 2-methyl-1-naphthol, 4-aminophenol and 2-methyl-5-aminophenol colors hair dark red. The shade obtained is very much similar to that of a commercially available dark red (see Example 4 of the present specification). The commercially available product's color ingredients are p-phenylenediamine, 4-aminophenol and 2-methyl-5-aminophenol.

The present invention relates to the use of 2-substituted-1-naphthols of the general formula I:

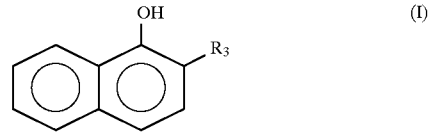

or salts thereof, preferably the sodium salt, wherein $R_3$ is $C_1$-$C_6$ alkyl or $C_1$-$C_6$ monohydroxyalkyl.

Preferred couplers in this preferred aspect of the invention are:

2-methyl-1-naphthol, 2-ethyl-1-naphthol,
2-propyl-1-naphthol, 2-hydroxymethyl-1-naphthol,
2-(2-hydroxyethyl)-1-naphthol,
2-(3-hydroxyethyl)-1-naphthol.

The aminophenol oxidation dye precursor (e.g. primary intermediate) useful in this invention comprise p-aminophenols, of the formula II:

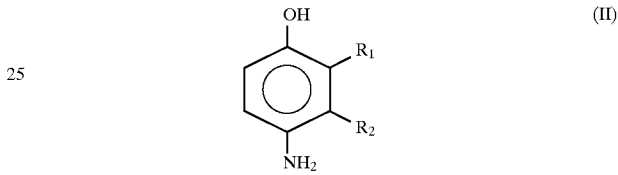

wherein $R_1$ and $R_2$ are each, independently, $C_1$-$C_6$ alkyl. Preferred primary intermediates include 2,3-dimethyl-4-aminophenol, 2,3-diethyl-4-aminophenol, and 2,3dipropyl-4-aminophenol.

The hair dye preparations of the present invention may be formulated into cosmetic preparations such as a solutions, creams, lotions, gels or emulsions. Also, in accordance with the invention, the compositions may contain a mixture of the coloring components (i.e., dye produced by coupling the dye intermediate with the coupling agent) along with other primary intermediates and/or couplers, as well as other components commonly associated with the formulation of solutions, creams, lotions, gels or emulsions, and the like. For example, components such as wetting agents or emulsifying agents from the categories of anionic or non-ionic surfactants, such as sulfates of fatty alcohols, alkanolamides of fatty alcohols, alkyl sulfonates, alkylbenzene sulfonates, oxyethylated fatty alcohols, oxyethylated nonylphenols. Thickeners, such a fatty alcohols, starch, cellulose derivatives, paraffin oil and fatty acids, as well as hair-care substances, such as lanolin derivatives, cholesterol and pantothenic acid, may be formulated into the compositions of the invention.

As used herein, unless indicated otherwise percent means percent by weight, based on total weight of the composition.

As an illustrative example, when formulated as a lotion, the compositions of the invention may contain organic solvents to assist in dissolving the dye precursors. Accordingly, the organic solvent content of the lotion may be from 0% to about 20%, preferably about 1% to 15%. Typically useful solvents include alcohols containing up to three carbon atoms, such as ethanol and isopropanol, polyhydroxy alcohols, such as propylene or hexylene glycol, and lower alkyl ethers thereof, such as ethoxy ethers.

In addition, the hair dyeing compositions in accordance with the present invention may optionally contain conventionally-used adjuvants and cosmetic additives, or mixtures thereof, to achieve the final formulations. Examples of such additives include, but are not limited to, anti-oxidants, e.g., ascorbic acid, erythorbic acid, or sodium sulfite to inhibit premature oxidizing; fragrances and/or perfume oils; chelating agents; emulsifiers; coloring agents; thickeners; organic solvents; opacifying agents; dispersing agents; sequestering agents; humectants; anti-microbials; and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, Cosmetics: *Science and Technology,* Vol. 2, Second Edition, (1972).

Thickeners that may be used in the compositions of the present invention include a variety of fatty acid soaps and associative polymeric thickeners. The fatty acid soaps are alkali metal salts or alkanolamine salts of fatty acids with $C_{10}$–$C_{16}$ alkyl side chains. The preferred fatty acids include oleic acid, myristic acid, stearic acid and lauric acid, which are generally present in the compositions of the invention at about 0.5% to 20%, preferably about 1% to 10%. Associative thickeners are polymers that can thicken solutions at low concentrations. Among the associative thickeners that are useful in the compositions of the present invention are acrylates copolymer (sold by Rohm and Haas under the trade name Aculyn-33), ceteareth-20 acrylates/steareth-20 methacrylate copolymer (sold by Rohm and Haas under the trade name Aculyn-22), acrylates/steareth-20 itaconate copolymer and acrylates/ceteth-20 itaconate copolymer. Another class of associative thickeners that is useful in the compositions of the present invention include the copolymers of polyurethane and polyethylene glycol or polyetherurethanes. One such illustrative material is sold by Rohm and Haas under the trade name Aculyn-44. The associative polymeric thickeners are generally present in the compositions of the invention at about 0.1% to 10%, preferably about 0.5% to 5%.

The oxidative coupling, i.e., the development of the dye, can, in principle, be performed with atmospheric oxygen to produce the final color product on the hair. However, chemical oxidation agents are suitably and preferably used. A preferred oxidizing agent for use as a developer or developing agent with primary intermediates and the couplers of the invention is hydrogen peroxide, although other peroxides may be employed. These include, for example, urea peroxide, melamine peroxide, perborates and percarbonates such as sodium perborate or percarbonate. The concentration of peroxide in the developer may be from about 0.5% to about 40%, preferably about 0.5% to 30%. If the preferred hydrogen peroxide is employed, the concentration will be from about 0.5% to about 12% by, preferably about 3% to 9%.

The compositions of the invention may include a typical anionic, cationic, nonionic or amphoteric surfactant.

The anionic surfactants include the variety of alkyl sulfates, alkylether sulfates, alkyl sulfonates, alkyl sulfosuccinates and N-acyl sarcosinates. The commonly-used anionic surfactants are sodium and ammonium lauryl sulfates, sodium and ammonium laurether sulfate and alpha olefin sulfonates. Anionic surfactants are generally present in the compositions of the present invention at about 0.1% to 15%, preferably about 0.5% to 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauramide DEA; lauramide MEA; isopropyl palmitate, isopropyl stearate and decylpolyglucoside. Nonionic surfactants are generally present in the compositions of the present invention at about 0.1% to 15%, preferably about 0.5% to 10%.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to 10%, preferably 0.5% to 5%.

Amphoteric surfactants maybe incorporated in the compositions of the present invention. Amphoteric surfactants that possess a positive and a negative charge in the same molecule and behave as a cation, an anion, or both, depending upon the pH of the medium and the nature of the amphoteric molecule. In general, the positive charge is located on a nitrogen, while the negative charge is carried by a carboxyl or sulfonate group. There are a large number of amphoteric surfactants that are suitable for use in the present invention, including, for example, the well-known betaines, sultaines, glycinates and propionates that may generally be represented by the following structural formulae:

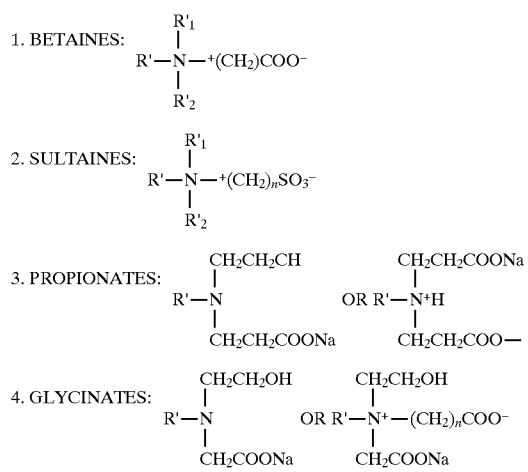

In these formulae, R' is an alkyl or alkylamide group containing from 10 to 20 carbon atoms. $R'_1$ and $R'_2$ are alkyl or hydroxyalkyl groups, which may be the same or different, and contain up to five carbon atoms. n is a positive integer from one to five.

The selection of the amphoteric surfactant or mixture of surfactants for use in the present compositions and methods is not critical. The surfactant may be selected from among those suggested above, or from any of a number of other known amphoteric surfactants. The amount of amphoteric surfactant in the compositions of the present invention is normally from about 0.5% to about 15%, preferably about 2% to 10%.

Depending on the final formulated preparation, the compositions in accordance with invention may be weakly acidic, neutral or alkaline. In particular the pH of the prepared compositions can range from about 7 to 11. Preferred is a pH range of about 8 to 10. Any of a wide variety of alkaline reagents or acidifying agents can be used to adjust the pH of the hair coloring compositions. Such alkaline reagents include ammonium hydroxide, potassium, sodium or calcium hydroxide, sodium or potassium carbonate, sodium or potassium borate, sodium phosphate, sodium silicate, guanidine hydroxide, or any one of the alkylamines or alkanolamines, for example, ethylamine, triethylamine, tris(hydroxymethyl)methylamine, ethanolamine, diethanolamine, triethanolamine, aminomethylpropanol, aminomethylpropanediol and the like. The preferred alkaline reagents are ammonium hydroxide, sodium hydroxide, sodium carbonate and ethanolamine. With the reagents listed above, the selected pH will generally be achieved if the composition contains from about 0.1% to 15%, preferably about 0.5% to 5%, of an alkaline reagent.

The application of the dyeing components is carried out by methods familiar to those in the art, for example, by mixing the hair dyeing preparation with an oxidant shortly before use, or at the time of applying the mixture onto the hair. On the hair, the compositions preferably form a stable formulation with enough consistency and body to remain on the hair during the complete coloring period without dripping or running. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 10 to 45 minutes, preferably approximately 30 minutes), the composition is washed from the hair with an ordinary water rinse followed by a shampoo. The application temperature is in the range of about 15° C. to 50° C.

Those in the art will appreciate that the compositions and methods of the present invention are appropriate for the dyeing of keratinous fibers, including the hair fibers of animals and humans, with particular application to the oxidative coloring of human hair.

The compositions of this invention may be separately provided in a kit or packaged form ready for mixing by the user, either professional or personal, to initiate the dyeing process. The kit provided in accordance with this invention comprises containers for housing the developer (oxidizing agent) and the dye precursors, such as the primary intermediate(s) and coupler(s). In the most convenient form, there will be two containers, one containing the dye precursors, e.g., as a lotion; the other containing the oxidizing agent.

The method of the invention comprises applying a mixture of the dye precursors and developers and other additives if necessary or desired, to the hair to be colored and allowing the resultant composition mixture to remain in contact with the hair until the desired hair color has been attained, after which time the composition is removed from the hair as conventionally known.

The invention is further described by way of the examples below.

EXAMPLE 1

The following comparative compositions A and B were prepared.

TABLE 1

| Formulation of Compositions A and B | | |
|---|---|---|
| Composition | A (%) | B (%) |
| Water | 44.50 | 44.50 |
| Lactic acid | 10.00 | 10.00 |
| Monoethanolamine | 12.00 | 12.00 |
| Oleic acid | 0.50 | 0.50 |
| Cocamidopropyl betaine | 17.00 | 17.00 |
| Sodium sulfite | 0.10 | 0.10 |
| EDTA | 0.10 | 0.10 |
| Erythorbic acid | 0.40 | 0.40 |
| 2,3-Dimethyl-4-aminophenol | 1.37 | |
| 2,6-Dimethyl-4-aminophenol | | 1.37 |
| 2-Methyl-1-naphthol | 1.58 | 1.58 |
| Water | QS 100 | QS 100 |
| Color | Violet | Magenta |

100 g of the composition are mixed with 100 g of hydrogen peroxide (20 Volume). The resulting mixture is applied to bleached and gray hair and permitted to remain in contact with the hair for 30 minutes. The thus dyed hair is then shampooed and rinsed with water and dried. Tristimulus values are then determined using a Hunter Tristimulus Colorimeter. L is a measure of lightness and darkness (in other words, the depth of color of the hair tress). The a and b values indicate color directions: +a is in the red direction, −a is in the green direction, +b is in the yellow direction, −b is in the blue direction.

The same dyeing condition and color measurement were used throughout the study.

TABLE 2

Hunter Tristimulus values for hair dyed with composition A and hair dyed with composition B

| | | | Hunter Values | |
|---|---|---|---|---|
| Composition | Type of Fiber | L | a | b |
| A | Bleached | 15.35 | 16.84 | 1.67 |
| | Gray | 20.23 | 11.94 | 2.18 |
| | Wool | 24.81 | 21.04 | −2.78 |
| B | Bleached | 27.43 | 28.21 | 8.59 |
| | Gray | 18.11 | 13.54 | 4.41 |
| | Wool | 27.01 | 25.61 | 5.80 |

It should be noted that the Tristimulus b value derived from 2,3-dimethyl-4-aminophenol has lower number than that derived from 2,6-dimethyl-4-aminophenol. The less the b value is, the more the blue coloration is.

EXAMPLE 2

In order to compare 2,3-dimethyl-4-aminophenol and 2,6-dimethyl-4-aminophenol in the presence of other primary intermediates and couplers, the following compositions were prepared.

TABLE 3

Formulation of Compositions C and D

| | C (%) | D (%) |
|---|---|---|
| Water | 44.50 | 44.50 |
| Lactic acid | 10.00 | 10.00 |
| Monoethanolamine | 12.00 | 12.00 |
| Oleic acid | 0.50 | 0.50 |
| Cocamidopropyl betaine | 17.00 | 17.00 |
| Sodium sulfite | 0.10 | 0.10 |
| EDTA | 0.10 | 0.10 |
| Erythorbic acid | 0.40 | 0.40 |
| 2,3-Dimethyl-4-aminophenol | 0.69 | |
| 2,6-Dimethyl-4-aminophenol | | 0.69 |
| 2-Methyl-1-naphthol | 0.79 | 0.79 |
| 4-Aminophenol | 0.55 | 0.55 |
| 2-Methyl-5-aminophenol | 0.62 | 0.62 |
| Water | QS 100 | QS 100 |
| Color | Red | Orange Red |

The dyeing procedure and conditions described in Example 1 above were used for the evaluation of the compositions C and D. The dyeing results are shown in Table 4.

TABLE 4

Hunter Tristimulus values for hair dyed with composition C and hair dyed with composition D

| | | | Hunter Values | |
|---|---|---|---|---|
| Composition | Type of Fiber | L | a | b |
| C | Bleached | 17.77 | 19.13 | 6.58 |
| | Gray | 23.16 | 10.47 | 5.93 |
| | Wool | 27.22 | 22.01 | 5.85 |
| D | Bleached | 23.62 | 27.35 | 11.59 |
| | Gray | 22.70 | 11.23 | 7.47 |
| | Wool | 27.75 | 23.50 | 10.74 |

The smaller b values for the C composition is due to the presence of 2,3-dimethyl-4-aminophenol.

EXAMPLE 4

TABLE 5

Formulation of Compositions E and F (a commercially available product)

| | E (%) | F (%) |
|---|---|---|
| Water | 44.50 | Commercial Product contains 4-aminophenol, p-phenylenediamine, and 2-methyl-5-aminophenol. |
| Lactic acid | 10.00 | |
| Monoethanolamine | 12.00 | |
| Oleic acid | 0.50 | |
| Cocamidopropyl betaine | 17.00 | |
| Sodium sulfite | 0.10 | Dyeing time was 20 min. |
| EDTA | 0.10 | |
| Erythorbic acid | 0.40 | |
| 2,3-dimethyl-4-aminophenol | 2.06 | |
| 4-Aminophenol | 0.55 | |
| 2-Methyl-1-naphthol | 2.37 | |
| 2-Methyl-S-aminophenol | 0.62 | |
| Water | QS 100 | Dark red |
| Color | Dark red | Dark red |

TABLE 6

Hunter Tristimulus values for hair dyed with composition E and hair dyed with composition F

| | | | Hunter Values | |
|---|---|---|---|---|
| Composition | Type of Fiber | L | a | b |
| E | Bleached | 12.75 | 7.66 | 2.31 |
| | Gray | 17.72 | 10.40 | 2.99 |
| F | Bleached | 17.41 | 13.43 | 4.59 |
| | Gray | 17.52 | 11.33 | 3.57 |

Composition E and commercial product F impart the same shade coloration to gray hair. In Table 6 this is well demonstrated by the Hunter values shown in italic bold fonts.

We claim:

1. In an oxidative dye composition for dyeing a keratin fiber, the composition containing a primary intermediate, a coupler, and a cosmetically acceptable vehicle, the primary intermediate and the coupler being present in respective amounts such that in the presence of an oxidizing agent they react to produce a tinctorially effective amount of a dye, the improvement comprising the coupler is a 2-substituted-1-naphthol compound having the formula I

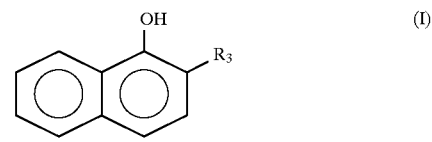

wherein $R_3$ is $C_1$–$C_6$ alkyl or monohydroxy $C_1$–$C_6$-alkyl and the primary intermediate is a compound of the formula II:

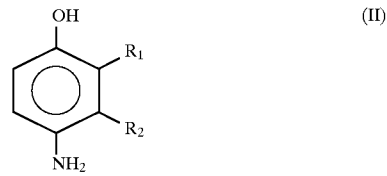

wherein $R_1$ and $R_2$ are each independently $C_1$–$C_6$ alkyl.

2. The composition according to claim 1, wherein the compound of formula I is selected from the group consisting of 2-methyl-1-naphthol, 2-ethyl-1-naphthol, 2-propyl-1-naphthol, 2-hydroxymethyl-1-naphthol, 2-(2-hydroxyethyl)-1-naphthol and 2-(3-hydroxypropyl)-1-naphthol.

3. The composition of claim 1, wherein the primary intermediate is 2,3-dimethyl-4-aminophenol, 2,3-diethyl-4-aminophenol, or 2,3-dipropyl-4-aminophenol.

4. The composition according to claim 1, wherein the primary intermediate is 2,3-dimethyl-4-aminophenol and the coupler is 2-methyl-1-naphthol.

5. In a method for dyeing hair including the steps of reacting a primary intermediate with a coupler in the presence of an oxidizing agent to produce a tinctorially effective amount of an oxidation hair dye and contacting a hair fiber with a composition containing said dye, the improvement comprising the coupler is a 2-substituted-1-naphthol compound having the formula I

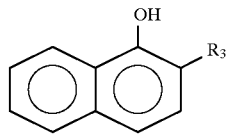

wherein $R_3$ is $C_1$–$C_6$ alkyl or monohydroxy $C_1$–$C_6$-alkyl, and the primary intermediate is a compound of the formula II:

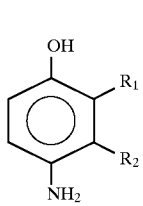

wherein $R_1$ and $R_2$ are each independently $C_1$–$C_6$ alkyl.

6. The method according to claim 5, wherein the compound of formula I is selected from the group consisting of 2-methyl-1-naphthol, 2-ethyl-1-naphthol, 2-propyl-1-naphthol, 2-hydroxymethyl-1-naphthol, 2-(2-hydroxyethyl)-1-naphthol and 2-(3-hydroxypropyl)-1-naphthol.

7. The method according to claim 5, wherein the primary intermediate is 2,3-dimethyl-4-aminophenol.

8. The method according to claim 5, wherein the primary intermediate is 2,3-dimethyl-4-aminophenol and the coupler of formula I is 2-methyl-1-naphthol.

9. The composition according to claim 1, further containing at least one material selected from the group consisting of perfumes, antioxidants, sequestering agents, alkalizing agents, acidifying agents and developers.

10. The composition according to claim 1, further containing at least one other primary intermediate or coupler other than I or II.

11. The method of claim 5, wherein the composition further contains at least one other primary intermediate or coupler other than I or II.

* * * * *